United States Patent
Kakizaki

(10) Patent No.: US 8,088,343 B2
(45) Date of Patent: Jan. 3, 2012

(54) AUTOMATIC ANALYZER

(75) Inventor: Kenichi Kakizaki, Mishima (JP)

(73) Assignee: Beckman Coulter, Inc., Brea, CA (US)

( * ) Notice: Subject to any disclaimer, the term of this patent is extended or adjusted under 35 U.S.C. 154(b) by 562 days.

(21) Appl. No.: 12/249,432

(22) Filed: Oct. 10, 2008

(65) Prior Publication Data

US 2009/0041628 A1    Feb. 12, 2009

Related U.S. Application Data

(63) Continuation of application No. PCT/JP2007/058511, filed on Apr. 19, 2007.

(30) Foreign Application Priority Data

May 11, 2006  (JP) .................................. 2006-132555

(51) Int. Cl.
*B01L 99/00* (2010.01)
*G01N 21/00* (2006.01)

(52) U.S. Cl. ......................................... 422/546; 422/63

(58) Field of Classification Search .................. 422/546, 422/63
See application file for complete search history.

(56) References Cited

U.S. PATENT DOCUMENTS

| | | | |
|---|---|---|---|
| 5,540,081 A * | 7/1996 | Takeda et al. | 73/37 |
| 6,267,927 B1 * | 7/2001 | Pomar Longedo et al. | 422/65 |
| 2004/0005245 A1 * | 1/2004 | Watson et al. | 422/65 |
| 2004/0265185 A1 * | 12/2004 | Kitagawa | 422/100 |

FOREIGN PATENT DOCUMENTS

JP           05142235 A      6/1993

* cited by examiner

*Primary Examiner* — Lore Jarrett
(74) *Attorney, Agent, or Firm* — Kilpatrick Townsend & Stockton LLP

(57) ABSTRACT

An automatic analyzer includes a wastewater suction unit that causes a suction nozzle to suction a reaction wastewater from each of plural reaction vessels transferred to a disposal position, transfers the plural suction nozzles to a cleaning position to make the suction nozzles suction a cleaning liquid, and clean the suction nozzles. The wastewater suction unit includes a pressure detector that is arranged near the suction nozzle in a pipe that guides a negative pressure for suction to each of the suction nozzles to detect pressure in each of the suction nozzles at time of suctioning of the reaction wastewater, a vessel determination unit that determines whether the reaction vessel is present or not at the disposal position, and a clog determination unit that determines whether each of the suction nozzles is clogged or not based on change in pressure in the suction nozzle and presence/absence of the reaction vessel.

3 Claims, 5 Drawing Sheets

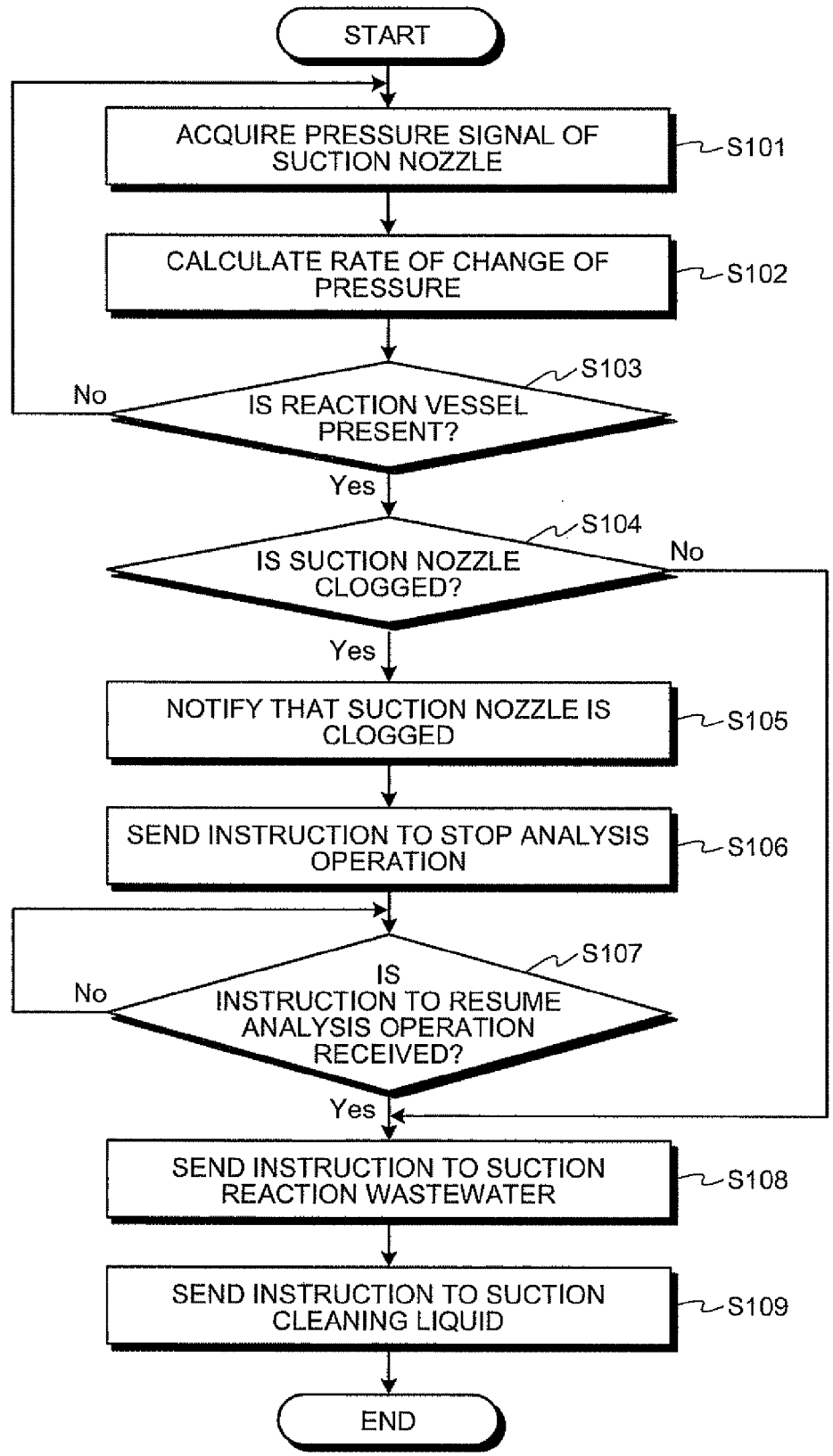

ical analyzer which includes a wastewater suction unit and is employed for biochemical testing, gene testing, and immunological testing and more particular to an automatic analyzer which includes a wastewater suction unit which is applicable to a liquid containing a magnetic particle.

2. Description of the Related Art

Conventional automatic analyzers, which analyze biological specimens such as blood, analyze components, concentration, and the like of a sample by mixing the sample and a reagent in a reaction vessel to cause reaction and optically measuring an obtained reaction liquid. Through the analysis, a reaction wastewater resulting from the reaction of the sample and the reagent is produced in the reaction vessel of the automatic analyzer. After the analysis, it is required to remove the reaction wastewater from the reaction vessel and clean the reaction vessel. Otherwise, the sample of the previous measurement blends into a sample of the next measurement to cause contamination. Then, a correct analysis value of the sample cannot be obtained. To deal with such problems, some automatic analyzers are provided with a wastewater suction unit which suctions and disposes of the reaction wastewater via a nozzle (see, for example Japanese Patent Application Laid-Open No. H5-142235).

SUMMARY OF THE INVENTION

An automatic analyzer according to one aspect of the present invention includes a wastewater suction unit that causes a suction nozzle to suction a reaction wastewater from each of plural reaction vessels transferred to a disposal position, transfers the plural suction nozzles to a cleaning position to make the suction nozzles suction a cleaning liquid, and thereby cleans the plural suction nozzles, and the wastewater suction unit includes a pressure detector that is arranged near the suction nozzle in a pipe that guides a negative pressure for suction to each of the suction nozzles to detect pressure in each of the suction nozzles at time of suctioning of the reaction wastewater, a vessel determination unit that determines whether the reaction vessel is present or not at the disposal position, and a clog determination unit that determines whether each of the suction nozzles is clogged or not based on change in pressure in the suction nozzle and presence/absence of the reaction vessel.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 7 is a flowchart for explaining determination procedures executed under the control of a control device to determine whether each suction nozzle is clogged or not.

DETAILED DESCRIPTION OF THE PREFERRED EMBODIMENTS

Figure 1:
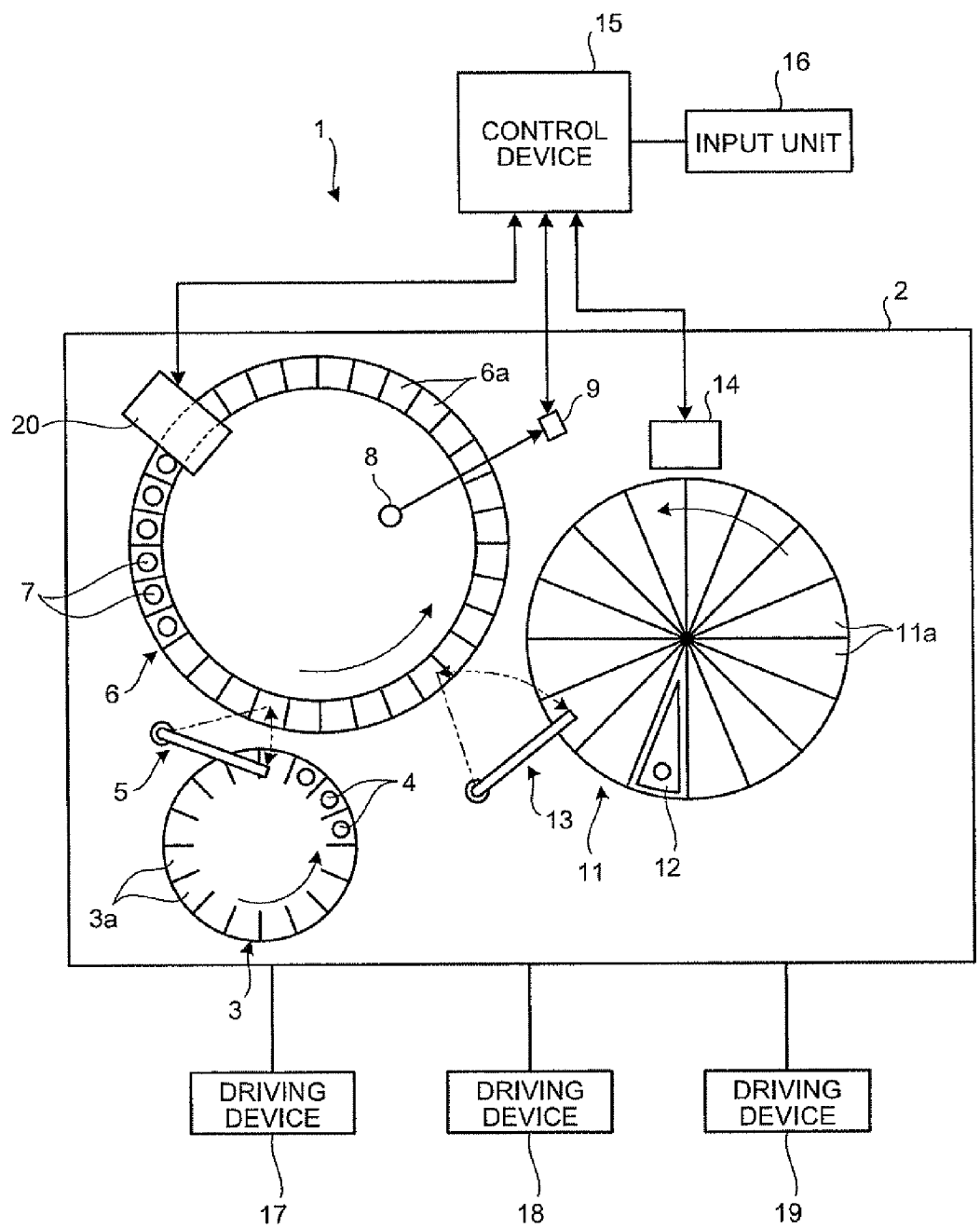
FIG. 1 is a schematic configuration diagram of an example of an automatic analyzer according to one embodiment of the present invention.
Figure 2:
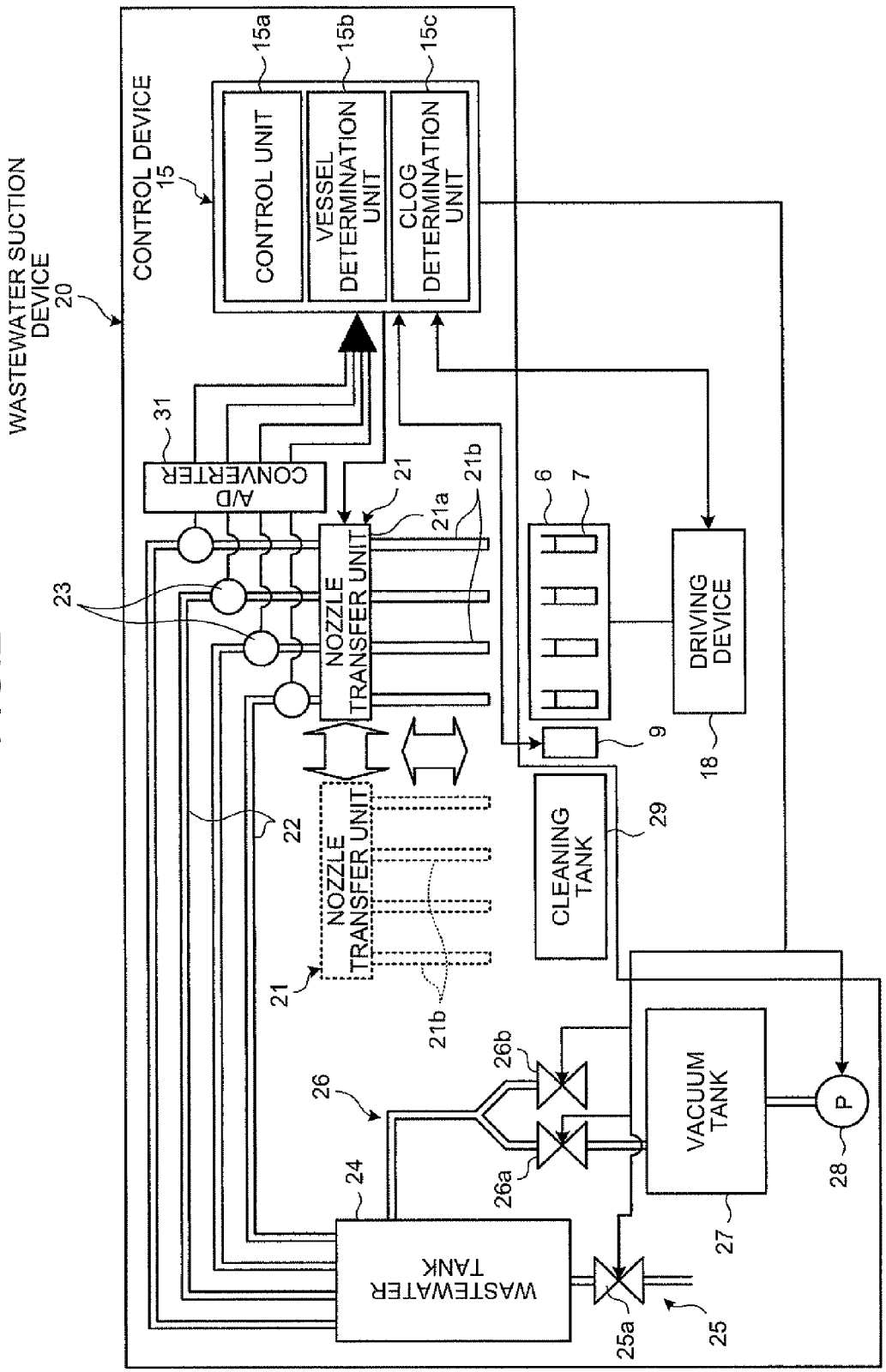
FIG. 2 is a schematic configuration diagram of a wastewater suction device employed in the automatic analyzer of FIG. 1.

Exemplary embodiments of an automatic analyzer according to the present invention are described in detail below with reference to the accompanying drawings. FIG. 1 is a schematic configuration diagram of an example of the automatic analyzer of the present invention. FIG. 2 is a schematic configuration diagram of a wastewater suction device employed in the automatic analyzer of FIG. 1.

An automatic analyzer 1 includes, as shown in FIG. 1, an operation table 2 on which a sample table 3, a reaction table 6, and a reagent table 11 are arranged separate from each other so that each can rotate in a circumferential direction and be positioned freely. Further, the automatic analyzer 1 includes a sample-dispensing arm 5 near the sample table 3 and the reaction table 6, and a reagent-dispensing arm 13 for dispensing a reagent near the reaction table 6 and the reagent table 11.

The sample table 3 is rotated by a driving device 17 in a direction indicated by an arrow as shown in FIG. 1. Along an outer periphery of the sample table 3, plural storage units 3a are arranged equiangularly along the circumferential direction. In each of the storage units 3a, a sample vessel 4 holding a sample is detachably stored.

The sample-dispensing arm 5 sequentially dispenses the samples in the plural sample vessels 4 on the sample table 3 into a reaction vessel 7.

Along an outer periphery of the reaction table 6, plural storage units 6a are arranged equiangularly along a circumferential direction as shown in FIG. 1. The reaction table 6 is rotated by a driving device 18 such as a pulse motor in a direction indicated by an arrow. On the reaction table 6, the reaction vessel 7 is detachably stored in each storage unit 6a to cause reaction of the sample and the reagent. Further, on the reaction table 6, a light source 8 and a wastewater suction device 20 are arranged. The light source 8 emits analyzing light (of 340 nm to 800 nm) for analyzing a reaction liquid produced by the reaction of the reagent and the sample in the reaction vessel 7. The analyzing light emitted from the light source 8 transmits the reaction liquid in each reaction vessel 7 transferred by the reaction table 6 rotating in the direction indicated by the arrow, and is received by a light-receiving device 9 arranged opposite to the light source 8. The light-receiving device 9 is connected to a control device 15 which calculates components, concentration, and the like of the sample based on an absorbance of the reaction liquid in each reaction vessel 7.

The reagent table 11 is rotated by a driving device 19 in a direction indicated by an arrow as shown in FIG. 1. On the reagent table 11, plural storage units 11a formed in a fan-like shape are arranged along a circumferential direction. In each storage unit 11a, a reagent vessel 12 is detachably stored. The plural reagent vessels 12 are each filled with a predetermined reagent corresponding to a test item, and an information label is pasted onto an outer surface of the reagent vessel 12 to indicate information related to the stored reagent.

External to the outer circumference of the reagent table 11, a reader device 14 is arranged. The reader device 14 reads the information recorded in the information label pasted on the reagent vessel 12, such as a type, a lot, and an expiration date of the reagent, an identification number of the reagent vessel 12, and the like and outputs the read-out information to the control device 15.

The control device 15 includes a control unit 15a, a vessel determination unit 15b, and a clog determination unit 15c. The control device 15 controls the operation of the automatic analyzer 1 based on information input by an input unit 16. The control unit 15a has a timer function, and controls the operations of the sample-dispensing arm 5, the light-receiving device 9, the reagent-dispensing arm 13, the reader device 14, the driving devices 17 to 19, and the wastewater suction device 20. The vessel determination unit 15b calculates components, concentration, and the like of the sample in the reaction vessel 7 based on optical signals output from the light-receiving device 9 concerning the amount of received light, and determines whether there is the reaction vessel 7 or not, and further associates with a position on the reaction table 6 for which the presence/absence of the reaction vessel 7 is detected based on pulse signals output from the driving device 18. The vessel determination unit 15b determines whether there is the reaction vessel 7 or not utilizing the above results, when the reaction vessel 7 is transferred to the position of the wastewater suction device 20 and the suction nozzle 21b is clogged. The clog determination unit 15c calculates rate of change ($\Delta P/\Delta t$) in pressure (P) based on a pressure signal output from a pressure sensor 23 for the suction nozzle 21b and determines whether each suction nozzle 21b is clogged or not based on the rate of change of pressure as calculated and the presence/absence of the reaction vessel 7 determined by the vessel determination unit 15b.

The wastewater suction device 20 is arranged at a disposal position on the outer periphery of the reaction table 6. As shown in FIG. 2, the wastewater suction device 20 includes a nozzle transfer unit 21, a wastewater tank 24, a vacuum tank 27, and a cleaning tank 29, and shares the control device 15 with the automatic analyzer 1.

The nozzle transfer unit 21 supports plural suction nozzles 21b on a main body 21a and moves the plural suction nozzles 21b in an up-down direction and a horizontal direction under the control of the control device 15 so that the plural suction nozzles 21b are alternately transferred between the reaction table 6 and the cleaning tank 29.

The wastewater tank 24 is connected to the respective suction nozzles 21b of the nozzle transfer unit 21 by pipes 22. Reaction wastewater suctioned by the plural suction nozzles 21b from the reaction vessel 7 and a cleaning liquid suctioned from the cleaning tank 29 are disposed in the wastewater tank 24. The pressure sensor 23 is arranged in each of the pipes 22 separately. Pressure (analog signal) detected by the pressure sensor 23 is converted into a digital pressure signal by an A/D converter 31 and output to the control device 15. The wastewater tank 24 is connected to a drain pipe 25 to which a drain valve 25a is attached. Because each of the pressure sensors 23 is arranged in the pipe 22 near the suction nozzle 21b and the pipes 22 guide negative pressure to the suction nozzle 21b for suction, the pressure sensor 23 can detect pressure variation in the suction nozzle 21b in real time, in other words, the pressure sensor 23 can detect the clog of each suction nozzle 21b in real time. The wastewater tank 24 can drain the wastewater through the drain pipe 25 by closing a suction valve 26a and opening the drain valve 25a and an air open valve 26b.

The vacuum tank 27 is connected to the wastewater tank 24 by a pipe 26 to which the suction valve 26a is attached. The pipe 26 is branched in the middle, and the air open valve 26b is attached to a branched part. Further, the vacuum tank 27 is connected to a suction pump 28. Operations of the drain valve 25a, the suction valve 26a, the air open valve 26b, and the suction pump 28 are controlled by the control device 15. When the reaction wastewater and the cleaning liquid are suctioned, the drain valve 25a and the air open valve 26b are closed.

The cleaning tank 29 is arranged near the reaction table 6, and stores a cleaning liquid for cleaning the plural suction nozzles 21b after the suction of the reaction wastewater.

Figure 3:
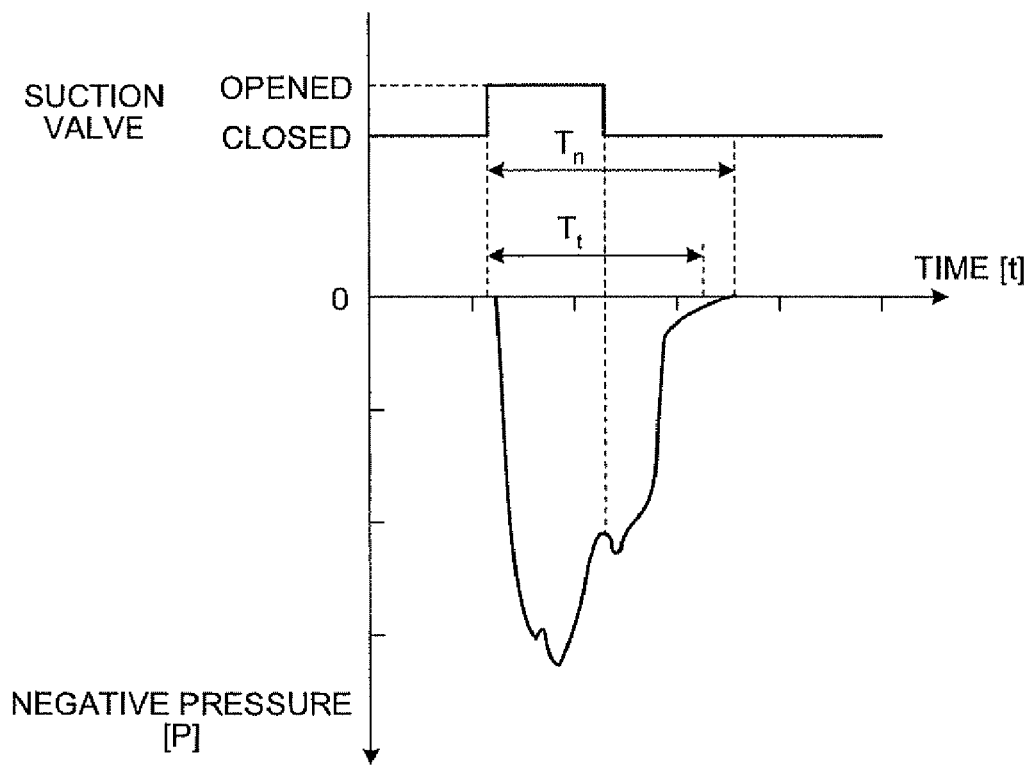
FIG. 3 is a waveform diagram of a pressure signal detected by a pressure sensor when a suction nozzle which suctions a reaction wastewater is not clogged.
Figure 4:
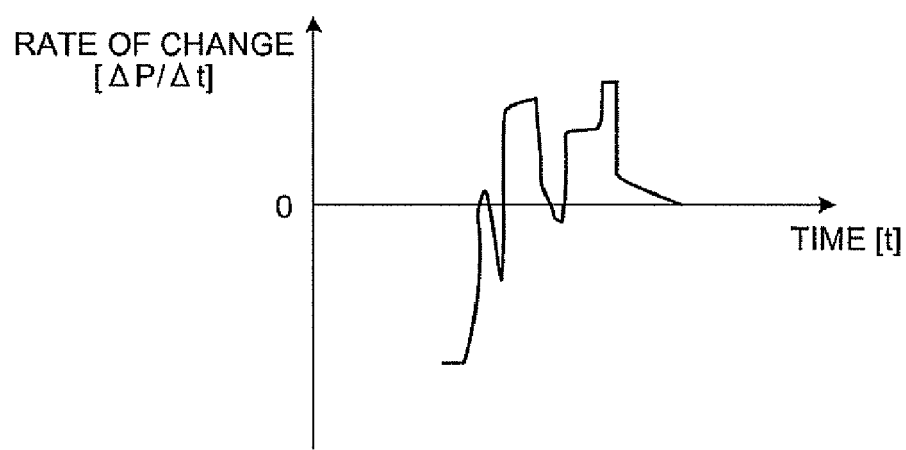
FIG. 4 is a graph of rate of change of pressure calculated based on the waveform of the pressure signal shown in FIG. 3.

In the wastewater suction device 20, when the suction pump 28 is driven to render the pressure in the vacuum tank 27 negative and the suction valve 26a is opened for a predetermine period of time, the negative pressure in the vacuum tank 27 is guided through the wastewater tank 24 and the pipes 22 to the plural suction nozzles 21b. Therefore, when the suction nozzle 21b, which suctions the reaction wastewater in the reaction vessel 7, is not clogged, the pressure in the suction nozzle 21b suddenly becomes negative within a short period of time after the suction valve 26a is opened, and the suction nozzle 21b suctions the reaction wastewater. When the suction valve 26a is closed, the pressure in the suction nozzle 21b gradually increases and returns to the atmospheric pressure. Because the pressure sensor 23 is arranged near the suction nozzle 21b in the pipe 22, the pressure sensor 23 detects the pressure variation in the suction nozzle 21b in real time. Therefore, when the suction valve 26a is opened, the pressure signal input to the control device 15 based on the pressure detected by the pressure sensor 23 shows a waveform with a large peak value variation as shown in FIG. 3. The rate of change of pressure calculated by the clog determination unit 15c based on the pressure signal shown in FIG. 3 exhibits large negative/positive variations as shown in FIG. 4.

Figure 5:
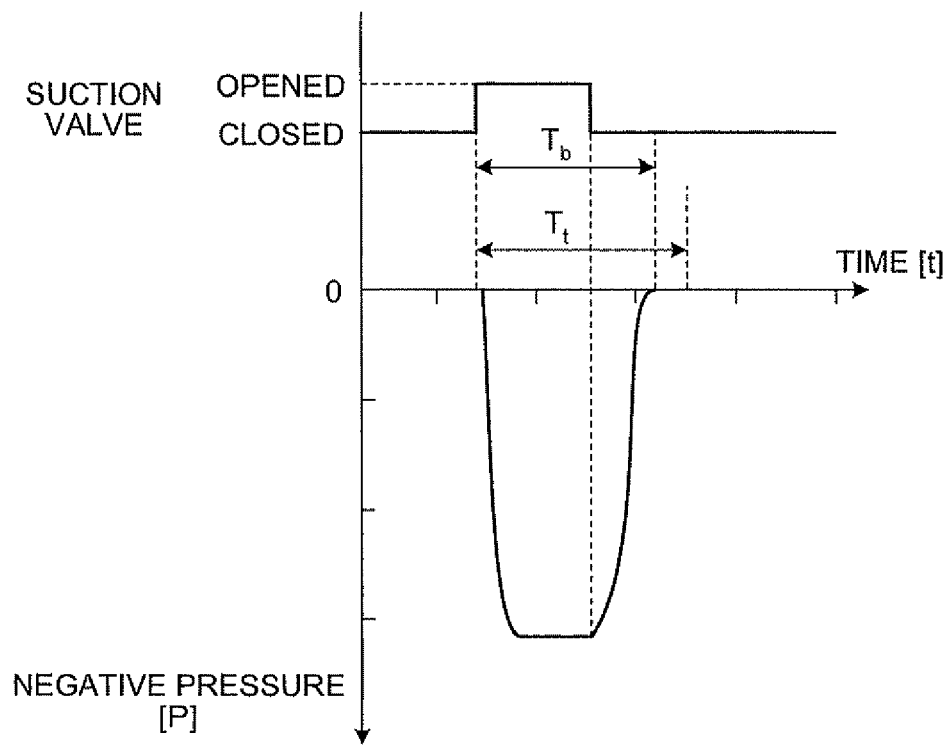
FIG. 5 is a waveform diagram of a pressure signal detected by the pressure sensor when a suction nozzle which suctions a reaction wastewater is clogged.
Figure 6:
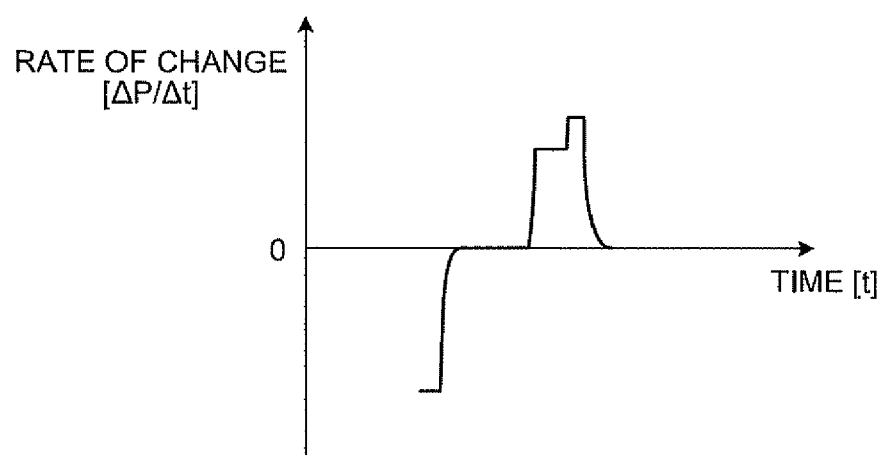
FIG. 6 is a graph of rate of change of pressure calculated based on the waveform of the pressure signal shown in FIG. 5.

On the other hand, when the suction nozzle 21b is clogged, the pressure in the suction nozzle 21b suddenly turns to a predetermined negative level within a short period of time after the suction valve 26a is opened. When the suction valve 26a is closed, the pressure in the suction nozzle 21b gradually increases and returns suddenly to the atmospheric pressure when other suction nozzle 21b is communicated with the atmosphere. Therefore, the pressure signal input to the control device 15 based on the pressure detected in real time by the pressure sensor 23 shows a waveform with a little peak value variation as shown in FIG. 5 when valve-opening time of the suction valve 26a is the same. The rate of change of pressure calculated by the clog determination unit 15c shows a little negative/positive variation as shown in FIG. 6 in comparison with the time when the suction nozzle 21b is not clogged.

However, when there is no reaction wastewater to be suctioned, and the suction nozzle 21b suctions without effect, the waveform of the pressure signal input to the control device 15 based on the pressure detected by the pressure sensor 23 becomes similar to the waveform of FIG. 5 with a little peak value variation obtained when the nozzle is clogged. Therefore, the clog determination unit 15c adds to a factor for determination, the presence/absence of the reaction vessel 7 at the disposal position on the outer periphery of the reaction table 6, and determines whether each of the suction nozzles 21b is clogged or not based on the rate of change of pressure calculated by the clog determination unit 15c and the presence/absence of the reaction vessel 7 determined by the vessel determination unit 15b. Thus, the clog determination unit 15c distinguishes the waveform of FIG. 5 obtained when there is the reaction vessel 7 and the suction nozzle 21b is clogged from a waveform obtained when there is no reaction vessel 7 and the suction nozzle 21b suctions without effect.

When there is the reaction vessel 7 at the disposal position on the outer periphery of the reaction table 6 though there is no reaction wastewater to suction, the vessel determination unit 15b determines whether there is reaction wastewater or not based on the optical signal output from the light-receiving device 9. The clog determination unit 15c distinguishes a case where there is the reaction vessel 7 though there is no reaction wastewater to suction from a case where there is no reaction vessel 7 and no reaction wastewater to suction based on the result of determination on the presence/absence of the reaction wastewater.

The automatic analyzer 1 configured as described above sequentially dispenses the samples in the plural sample vessels 4 on the sample table 3 using the sample-dispensing arm 5 into the reaction vessel 7 transferred along the circumferential direction by the rotating reaction table 6. The reaction vessel 7 into which the sample is dispensed is transferred close to the reagent-dispensing arm 13 by the reaction table 6, and the reagent in a predetermined one of the reagent vessels 12 is dispensed. While the reaction vessel 7 into which the reagent is dispensed is transferred along the circumferential direction by the reaction table 6, the specimen and the reagent agitated and react with each other pass between the light source 8 and the light-receiving device 9. The reaction liquid in the reaction vessel 7 is subjected to photometry by the light-receiving device 9, and the control device 15 calculates the components, concentration, and the like of the reaction liquid based on the absorbance thereof. After the analysis is finished, the reaction vessel 7 is transferred to the disposal position. The wastewater suction device 20 drains the reaction wastewater after the reaction from the reaction vessel 7. Then, the reaction vessel 7 is cleaned by a cleaning device not shown, and used again for the analysis of the sample.

At the time of analysis of the sample, the wastewater suction device 20 render the pressure in the vacuum tank 27 negative by driving the suction pump 28 under the control of the control device 15. Then, the wastewater suction device 20 transfers the nozzle transfer unit 21 to the disposal position on the outer periphery of the reaction table 6, lowers the nozzle transfer unit 21 so that the lower end of the plural suction nozzles 21b is inserted into the reaction wastewater in the plural reaction vessels 7 by a predetermined amount, and opens the suction valve 26a for a predetermined period of time. Thus, in the wastewater suction device 20, the reaction wastewater after the measurement finishes is suctioned by the plural suction nozzles 21b from the plural reaction vessels 7 and drained to the wastewater tank 24.

Then, the wastewater suction device 20 raises the nozzle transfer unit 21 under the control of the control device 15 while keeping the suction vale 26a closed, and moves the nozzle transfer unit 21 in the horizontal direction to above the cleaning tank 29. Then, the wastewater suction device 20 lower the nozzle transfer unit 21 under the control of the control device 15 so that the lower end of the plural suction nozzles 21b is inserted into the cleaning liquid by a predetermined amount, and makes the plural suction nozzles 21b suction the cleaning liquid stored in the cleaning tank 29 by opening the suction valve 26a for a predetermined period of time. Thus, the plural suction nozzles 21b are cleaned by the suctioned cleaning liquid, and the cleaning liquid after the cleaning is drained to the wastewater tank 24. At the drainage of the reaction wastewater from the reaction vessel 7 and the cleaning of the suction nozzle 21b by the cleaning liquid after the drainage of the reaction wastewater in the wastewater suction device 20, the clog determination unit 15c determines whether each of the suction nozzles 21b is clogged or not based on the rate of change of pressure in the suction nozzle 21b as calculated and the presence/absence of the reaction vessel 7, as follows.

Process procedures executed under the control of the control device 15 to determine whether each of the suction nozzles 21b is clogged or not are described below with reference to a flowchart of FIG. 7.

The control device 15 firstly acquires the pressure signal of the suction nozzle 21b from each of the plural pressure sensors 23 (step S101). Then, the control device 15 calculates the rate of change ($\Delta P/\Delta t$) in pressure (P) based on the acquired pressure signal from each of the pressures sensors 23 (step S102).

Then, the control device 15 determines whether the reaction vessel 7 is present at the disposal position or not (step S103). The determination is performed by the vessel determination unit 15b based on the optical signal output from the light-receiving device 9. When it is determined that there is no reaction vessel 7 at the disposal position (No in step S103), the control device 15 returns to step S101 and acquires the pressure signal of the suction nozzle 21b. On the other hand, when the reaction vessel 7 is present at the disposal position (Yes in step S103), the control device 15 determines whether the suction nozzle 21b is clogged or not (step S104). The determination is made for each of the suction nozzles 21b based on the rate of change ($\Delta P/\Delta t$) in pressure calculated by the vessel determination unit 15b and the presence/absence of the reaction vessel 7 determined by the vessel determination unit 15b.

When it is determined that the suction nozzle 21b is not clogged (No in step S104), the control device 15 skips to step S108. On the other hand, when the suction nozzle 21b is clogged (Yes in step S104), the control device 15 notifies that the suction nozzle 21b is clogged (step S105). The notification is realized by displaying a position (number) of the suction nozzle 21b which is clogged on a display of the automatic analyzer 1 or by raising an alarm along with the display, for example.

Then, the control device 15 instructs the automatic analyzer 1 to stop the analysis operation (step S106). While the automatic analyzer 1 stops following the instruction, an operator exchanges the suction nozzle 21b which is clogged, or exchanges all of the plural suction nozzles 21b.

Then, the control device 15 determines whether an instruction to resume the analysis operation is given to the automatic analyzer 1 or not (step S107). When the instruction to resume the analysis operation is not given (No in step S107), the control device 15 determines again whether the instruction to resume the analysis operation is given or not (step S107). On the other hand, when the instruction to resume the analysis operation is given (Yes in step S107), the control device 15 instructs the wastewater suction device 20 to suction the reaction wastewater from the reaction vessel 7 because the suction of the reaction wastewater has not been finished for some reaction vessels 7 because of the clogging of the suction nozzle 21b (step S108).

Then, the control device 15 instructs the wastewater suction device 20 to suction the cleaning liquid (step S109). According to the instruction, the nozzle transfer unit 21 moves to the position of the cleaning tank 29 and suctions the cleaning liquid. Thus, the plural suction nozzles 21b are cleaned. Because the automatic analyzer 1 cleans the suction nozzles 21b by suctioning the cleaning liquid every time the suction nozzle 21b suctions the reaction wastewater, the clogging of the suction nozzles 21b, the pipes 22, and the pressure sensors 23 can be prevented from being caused by crystal generated through the reaction of the sample and the reagent.

The clog determination unit 15c employs the rate of change ($\Delta P/\Delta t$) in pressure calculated by the vessel determination unit 15b on determining whether each of the suction nozzles 21b is clogged or not. The clog determination unit 15c, however, may determine whether each of the suction nozzles 21b is clogged or not based on the presence/absence of the reaction vessel 7 and recovery time required for the pressure in the suction nozzle 21b to return to the atmospheric pressure after negative pressure is introduced into the suction nozzle 21b (time Tn in FIG. 3, and time Tb in FIG. 5) utilizing the timer function of the control unit 15a. In this case, the clog determination unit 15c determines that the suction nozzle 21b is not clogged when the reaction vessel 7 is present at the disposal position and recovery time Tn is longer than predetermined reference value Tt, whereas determines that the suction nozzle 21b is clogged when recovery time Tb is shorter than the reference value Tt.

In the above-described embodiment, the vessel determination unit 15b determines whether the reaction vessel 7 is present or not utilizing the optical signal output from the light-receiving device 9 without providing an additional detector. The vessel determination unit 15b can, however, utilize various types of elements, such as a contact and a sensor, as far as the vessel determination unit 15b can determine whether the reaction vessel 7 is present or not at the disposal position.

Further, the reaction vessel may be, other than the reaction vessel 7 described in the above embodiment, a microplate.

Because the clog determination unit determines whether each of the suction nozzles is clogged or not based on pressure variation in the suction nozzle detected by the pressure detector arranged near the suction nozzle and the presence/absence of the reaction vessel determined by the vessel determination unit, the automatic analyzer of the embodiment has an advantageous effect that it can determine in real time whether each of the suction nozzles is clogged or not distinguishing a case where the suction nozzle suctions without effect from a case where the suction nozzle is clogged.

Further, because the clog determination unit of the embodiment employs rate of change of pressure in the suction nozzle for determining whether each of the suction nozzles is clogged or not, there is an advantageous effect that it can be determined whether each of the suction nozzles is clogged or not with high accuracy.

Further, because the clog determination unit of the embodiment employs time of change elapses before the pressure in the suction nozzle returns from the introduced negative pressure to the atmospheric pressure for determining whether each of the suction nozzles is clogged or not, there is an advantageous effect that there is more factors for determining whether each of the suction nozzles is clogged or not.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An automatic analyzer comprising:
   a plurality of suction nozzles, each suction nozzle of the plurality of suction nozzles connected to a corresponding pipe configured to guide a negative pressure to the corresponding suction nozzle, wherein the plurality of suction nozzles are configured to be transferable between a disposal position and a cleaning position;
   a plurality of reaction vessels;
   a wastewater suction unit configured to generate the negative pressure such that the plurality of suction nozzles suction a reaction wastewater from each of the plurality of reaction vessels when the plurality of suction nozzles are in the disposal position, and suction a cleaning liquid when the plurality of suction nozzles are in the cleaning position, the wastewater suction unit including
      a plurality of pressure detectors, each pressure detector positioned near an associated suction nozzle of the plurality of suction nozzles in the corresponding pipe, and configured to detect pressure in each of the plurality of suction nozzles at time of suctioning of the reaction wastewater,
      a vessel determination unit configured to determine whether the plurality of reaction vessels are present or not at the disposal position, and
      a clog determination unit configured to determine whether each of the plurality of suction nozzles is clogged or not based on change in pressure detected by each of the plurality of pressure detectors and the presence or absence of the plurality of reaction vessels determined by the vessel determination unit.

2. The automatic analyzer according to claim 1, wherein the clog determination unit is further configured to employ a rate of change of pressure, as the change in pressure in the plurality of suction nozzles.

3. The automatic analyzer according to claim 1, wherein the clog determination unit is further configured to employ time of change in the pressure in the plurality of suction nozzles to return from the negative pressure introduced into the plurality of suction nozzles to an atmospheric pressure, as the change in pressure in the plurality of suction nozzles.

* * * * *